(12) United States Patent
Jaroch et al.

(10) Patent No.: US 7,417,056 B2
(45) Date of Patent: Aug. 26, 2008

(54) 5-SUBSTITUTED QUINOLINE AND ISOQUINOLINE DERIVATIVES, A PROCESS FOR THEIR PRODUCTION AND THEIR USE AS ANTI-INFLAMMATORY AGENTS

(75) Inventors: Stefan Jaroch, Berlin (DE); Hartmut Rehwinkel, Berlin (DE); Heike Schaecke, Berlin (DE); Norbert Schmees, Berlin (DE); Werner Skuballa, Berlin (DE); Jan Huebner, Berlin (DE); Orlin Petrov, Berlin (DE); Matthias Schneider, Berlin (DE); Christian Dinter, Berlin (DE)

(73) Assignee: Schering AG, Berlin (DE)

( * ) Notice: Subject to any disclaimer, the term of this patent is extended or adjusted under 35 U.S.C. 154(b) by 91 days.

(21) Appl. No.: 11/272,009

(22) Filed: Nov. 14, 2005

(65) Prior Publication Data

US 2006/0116396 A1   Jun. 1, 2006

Related U.S. Application Data

(60) Provisional application No. 60/676,945, filed on May 3, 2005, provisional application No. 60/628,550, filed on Nov. 18, 2004.

(30) Foreign Application Priority Data

Nov. 12, 2004  (DE) .................. 10 2004 055 633
Apr. 26, 2005  (DE) .................. 10 2005 020 331

(51) Int. Cl.
*C07D 405/02*  (2006.01)
*A61K 31/47*  (2006.01)

(52) U.S. Cl. ................. 514/310; 514/313; 546/143; 546/159

(58) Field of Classification Search ................. 546/143, 546/159; 514/310, 313
See application file for complete search history.

(56) References Cited

U.S. PATENT DOCUMENTS 6,897,224 B2   5/2005   Jaroch et al.

FOREIGN PATENT DOCUMENTS

| WO | WO 03/082827 A | 10/2003 |
| WO | WO 2004/063163 A | 7/2004 |
| WO | WO 2004/075864 A | 9/2004 |
| WO | WO 2005/090343 A | 9/2005 |

*Primary Examiner*—Zinna N Davis
(74) *Attorney, Agent, or Firm*—Millen, White, Zelano & Branigan, P.C.

(57) ABSTRACT

Compounds of general formula (IIa) or (IIb)

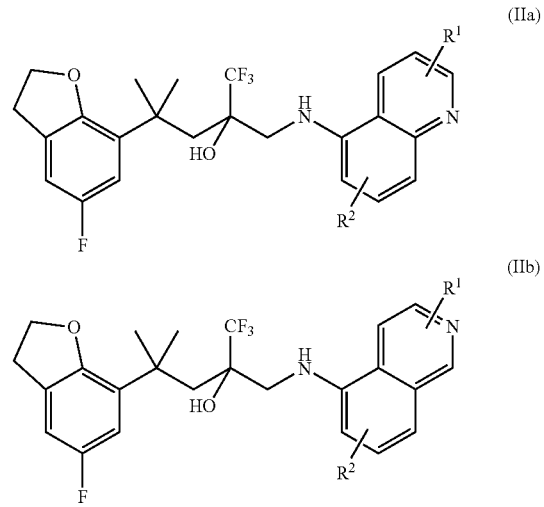

and their use as pharmaceutical agents.

32 Claims, No Drawings

5-SUBSTITUTED QUINOLINE AND ISOQUINOLINE DERIVATIVES, A PROCESS FOR THEIR PRODUCTION AND THEIR USE AS ANTI-INFLAMMATORY AGENTS

This application claims the benefit of the filing date of U.S. Provisional Application Ser. No. 60/628,550 filed Nov. 18, 2004 and U.S. Provisional Application Ser. No. 60/676,945 filed May 3, 2005, both of which are incorporated by reference herein.

The invention relates to 5-substituted quinoline and isoquinoline derivatives, a process for their production and their use as anti-inflammatory agents.

From the prior art WO03/082827, anti-inflammatory agents of general formula

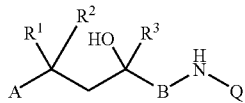

are known, whereby the Q-radical comprises quinoline and isoquinoline derivatives. In the experiment, these compounds show dissociations of actions between anti-inflammatory actions and undesirable metabolic actions and are superior to the previously described, nonsteroidal glucocorticoids or have at least just as good an action. Moreover, these compounds have improved selectivity compared to other steroid receptors.

It has now been found, surprisingly enough, that compounds of formulas (IIa) and (IIb) are especially active and are dissociated with respect to side effects and are preferably suitable for local administration.

This invention therefore relates to compounds of general formulas (IIa) and (IIb)

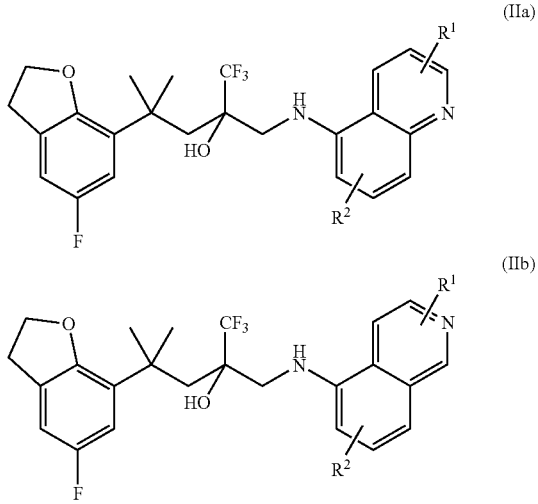

in which
 $R^1$ and $R^2$, independently of one another, can be a hydrogen atom, a $C_{1-3}$-alkyl group, a halogen atom, a cyano group, a $C_{1-3}$-alkoxy group or a hydroxy group, as well as their racemates or separately present stereoisomers and optionally their physiologically compatible salts or their prodrugs.

The designation halogen atom or halogen means a fluorine, chlorine, bromine or iodine atom. A fluorine, chlorine or bromine atom is preferred.

The $C_1$-$C_3$-alkyl groups and the $C_1$-$C_5$-alkyl groups can be straight-chain or branched and stand for a methyl, ethyl, n-propyl, iso-propyl, n-butyl, iso-butyl, tert-butyl or n-pentyl, 2,2-dimethylpropyl, 2-methylbutyl or 3-methylbutyl group.

A methyl or ethyl group is preferred.

Radicals $R^1$ and $R^2$ preferably mean hydrogen, $C_{1-3}$-alkyl, halogen or hydroxy. Especially preferred are hydrogen, methyl, chlorine and hydroxy.

Thus, a special subject of the invention relates to compounds of general formulas IIa and IIb, in which $R^1$ and $R^2$, independently of one another, preferably mean hydrogen, $C_{1-3}$-alkyl, halogen or hydroxy.

Compounds of formulas I and IIb, in which $R^1$ and $R^2$, independently of one another, mean hydrogen, methyl, chlorine or hydroxy, are especially preferred.

One special aspect of this invention are the compounds of general formula IIa.

The term "local" comprises any possible administration of the compounds according to the invention that makes possible direction penetration of the active ingredient at the site of action.

The compounds of general formulas (IIa) und (IIb) according to the invention can be present as different stereoisomers because of the presence of asymmetry centers. Both the racemates and the separately present stereoisomers belong to the subject of this invention.

The separately present stereoisomers, i.e., (+)-enantiomers and (−)-enantiomers, in particular of Examples 1, 2, 3, 4, 5, 11 and 12, are a special subject of this invention.

The compounds according to the invention, if they contain a hydroxy group in α-position to the quinolinyl- or isoquinolinyl-nitrogen atom, are also distinguished by the presence of a keto-enol-tautomerism. In terms according to the invention, both forms are part of the subject of the invention, even if, e.g., in the experimental part, only one of the two tautomeric forms has been cited.

In particular, subjects of this invention are:
5-[4-(5-Fluoro-2,3-dihydrobenzofuran-7-yl)-2-hydroxy-4-methyl-2-trifluoromethyl-pentylamino]-2-methylquinoline,
5-[4-(5-Fluoro-2,3-dihydrobenzofuran-7-yl)-2-hydroxy-4-methyl-2-trifluoromethyl-pentylamino]-1-methylisoquinoline),
5-[4-(5-Fluoro-2,3-dihydrobenzofuran-7-yl)-2-hydroxy-4-methyl-2-trifluoromethyl-pentylamino]isoquinol-1(2H)-one,
5-[4-(5-Fluoro-2,3-dihydrobenzofuran-7-yl)-2-hydroxy-4-methyl-2-trifluoromethyl-pentylamino]-2,6-dimethylquinoline,
5-[4-(5-Fluoro-2,3-dihydrobenzofuran-7-yl)-2-hydroxy-4-methyl-2-trifluoromethyl-pentylamino]-6-chloro-2-methylquinoline,
5-[4-(5-Fluoro-2,3-dihydrobenzofuran-7-yl)-2-hydroxy-4-methyl-2-trifluoromethyl-pentylamino]isoquinoline,
5-[4-(5-Fluoro-2,3-dihydrobenzofuran-7-yl)-2-hydroxy-4-methyl-2-trifluoromethyl-pentylamino]quinoline,
5-[4-(2,3-Dihydro-5-fluoro-7-benzofuranyl)-2-hydroxy-4-methyl-2-trifluoromethyl-pentylamino]quinolin-2[1H]-one, 6-Fluoro-5-[4-(5-fluoro-2,3-dihydrobenzofuran-7-yl)-2-hydroxy-4-methyl-2-trifluoromethyl-pentylamino]-2-methylquinoline,
8-Fluoro-5-[4-(5-fluoro-2,3-dihydrobenzofuran-7-yl)-2-hydroxy-4-methyl-2-trifluoromethyl-pentylamino]-2-methylquinoline,
5-[4-(5-Fluoro-2,3-dihydrobenzofuran-7-yl)-2-hydroxy-4-methyl-2-trifluoromethyl-pentylamino]-2-methylisoquinol-1(2H)-one, as well as their separate enantiomers:
2(R)-5-[4-(5-Fluoro-2,3-dihydrobenzofuran-7-yl)-2-hydroxy-4-methyl-2-trifluoromethyl-pentylamino]-2-methylquinoline),
2(R)-5-[4-(5-fluoro-2,3-dihydrobenzofuran-7-yl)-2-hydroxy-4-methyl-2-trifluoromethyl-pentylamino]-1-methylisoquinoline,
2(R)-5-[4-(5-Fluoro-2,3-dihydrobenzofuran-7-yl)-2-hydroxy-4-methyl-2-trifluoromethyl-pentylamino]isoquinol-1(2H)-one,
2(R)-5-[4-(5-Fluoro-2,3-dihydrobenzofuran-7-yl)-2-hydroxy-4-methyl-2-trifluoromethyl-pentylamino]-2,6-dimethylquinoline,
2(R)-5-[4-(5-Fluoro-2,3-dihydrobenzofuran-7-yl)-2-hydroxy-4-methyl-2-trifluoromethyl-pentylamino]-6-chloro-2-methylquinoline,
2(R)-5-[4-(5-Fluoro-2,3-dihydrobenzofuran-7-yl)-2-hydroxy-4-methyl-2-trifluoromethyl-pentylamino]isoquinoline,
2(R)-5-[4-(5-Fluoro-2,3-dihydrobenzofuran-7-yl)-2-hydroxy-4-methyl-2-trifluoromethyl-pentylamino]quinoline,
2(R)-5-[4-(2,3-Dihydro-5-fluoro-7-benzofuranyl)-2-hydroxy-4-methyl-2-trifluoromethyl-pentylamino]quinolin-2[1H]-one,
2(R)-6-Fluoro-5-[4-(5-fluoro-2,3-dihydrobenzofuran-7-yl)-2-hydroxy-4-methyl-2-trifluoromethyl-pentylamino]-2-methylquinoline,
2(R)-8-Fluoro-5-[4-(5-fluoro-2,3-dihydrobenzofuran-7-yl)-2-hydroxy-4-methyl-2-trifluoromethyl-pentylamino]-2-methylquinoline,
2(R)-5-[4-(5-Fluoro-2,3-dihydrobenzofuran-7-yl)-2-hydroxy-4-methyl-2-trifluoromethyl-pentylamino]-2-methylquinol-1(2H)-one,
2(S)-5-[4-(5-Fluoro-2,3-dihydrobenzofuran-7-yl)-2-hydroxy-4-methyl-2-trifluoromethyl-pentylamino]-2-methylquinoline),
2(S)-5-[4-(5-Fluoro-2,3-dihydrobenzofuran-7-yl)-2-hydroxy-4-methyl-2-trifluoromethyl-pentylamino]-1-methylisoquinoline),
2(S)-5-[4-(5-Fluoro-2,3-dihydrobenzofuran-7-yl)-2-hydroxy-4-methyl-2-trifluoromethyl-pentylamino]isoquinol-1(2H)-one,
2(S)-5-[4-(5-Fluoro-2,3-dihydrobenzofuran-7-yl)-2-hydroxy-4-methyl-2-trifluoromethyl-pentylamino]-2,6-dimethylquinoline,
2(S)-5-[4-(5-Fluoro-2,3-dihydrobenzofuran-7-yl)-2-hydroxy-4-methyl-2-trifluoromethyl-pentylamino]-6-chloro-2-methylquinoline,
2(S)-5-[4-(5-Fluoro-2,3-dihydrobenzofuran-7-yl)-2-hydroxy-4-methyl-2-trifluoromethyl-pentylamino]isoquinoline,
2(S)-5-[4-(5-Fluoro-2,3-dihydrobenzofuran-7-yl)-2-hydroxy-4-methyl-2-trifluoromethyl-pentylamino]quinoline,
2(S)-5-[4-(2,3-Dihydro-5-fluoro-7-benzofuranyl)-2-hydroxy-4-methyl-2-trifluoromethyl-pentylamino]quinolin-2[1H]-one,
2(S)-6-Fluoro-5-[4-(5-fluoro-2,3-dihydrobenzofuran-7-yl)-2-hydroxy-4-methyl-2-trifluoromethyl-pentylamino]-2-methylquinoline,
2(S)-8-Fluoro-5-[4-(5-fluoro-2,3-dihydrobenzofuran-7-yl)-2-hydroxy-4-methyl-2-trifluoromethyl-pentylamino]-2-methylquinoline,
2(S)-5-[4-(5-Fluoro-2,3-dihydrobenzofuran-7-yl)-2-hydroxy-4-methyl-2-trifluoromethyl-pentylamino]-2-methylisoquinol-1(2H)-one.

Especially preferred is 5-[4-(5-fluoro-2,3-dihydrobenzofuran-7-yl)-2-hydroxy-4-methyl-2-trifluoromethyl-pentylamino]-2-methylquinoline and its separately present enantiomers 2-(R)-5-[4-(5-fluoro-2,3-dihydrobenzofuran-7-yl)-2-hydroxy-4-methyl-2-trifluoromethyl-pentylamino]-2-methylquinoline and 2-(S)-5-[4-(5-fluoro-2,3-dihydrobenzofuran-7-yl)-2-hydroxy-4-methyl-2-trifluoromethyl-pentylamino]-2-methylquinoline.

The process for the production of the compounds of WO98/54159, WO00/32584 and WO02/10143 can also be used for the production of the compounds according to the invention. For the linkage of the quinoline or isoquinoline group that is characteristic of the compounds according to the invention, the following process steps can be implemented:

Title compounds (IIa) and (IIb) can be synthesized by, for example, reductive amination of the compound of formula (III) with 5-aminoquinolines or 5-aminoisoquinolines, whereby, e.g., sodium borohydride or sodium cyanoborohydride are considered to be reducing agents in the presence of an acid.

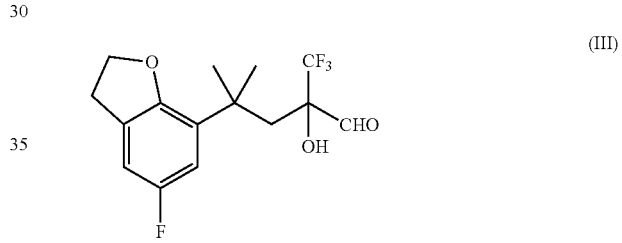
(III)

The synthesis of aldehyde is accomplished, for example, starting from compound (IV) (WO0032584) by cleavage of the methyl ether, allylation of the resulting phenol (V), rearrangement of allyl ether (VI) to (VII), dihydroxylation and glycol cleavage of the double bond with formation of lactol (VIII), reduction of lactol to diol (IX), ring closure to dihydrobenzofuran (X), reduction of ester to alcohol (XI), which finally is oxidized to aldehyde (III).

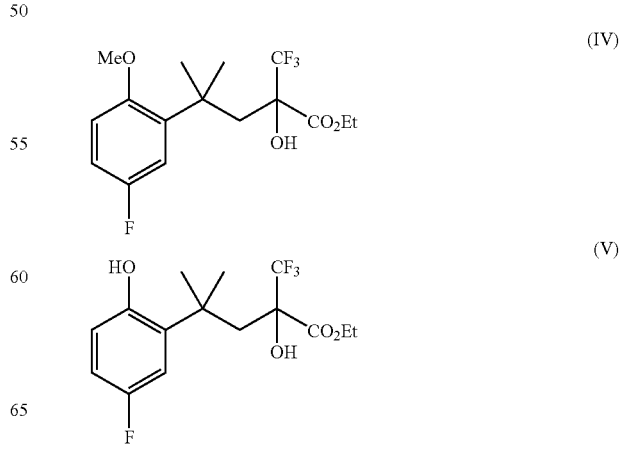

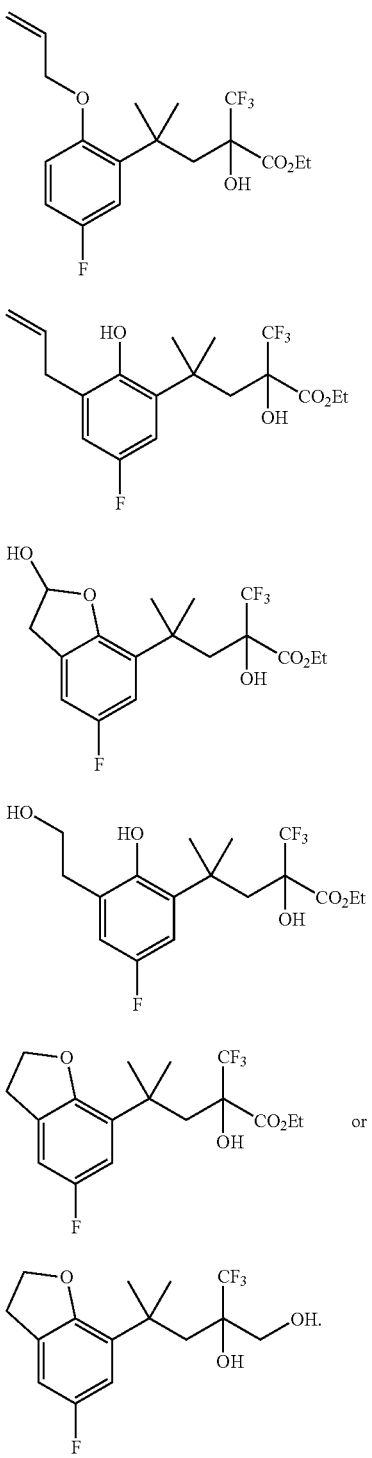

The above-cited esters are preferably ethyl esters but can be esters of type —COOR³, whereby R³ means $C_1$-$C_5$-alkyl.

A special subject of the invention is the production of compounds of general formulas (IIa) and (IIb), by the aldehyde (III) being reacted under conditions of reductive amination, optionally in two stages, with a 5-aminoquinoline derivative or a 5-aminoisoquinoline derivative whereby $R^1$ and $R^2$ have the meanings that are indicated for the compounds of formulas IIa and IIb in claim 1.

Another subject of the invention is the production of aldehyde (III), which can be obtained by reduction of the compound of general formula X—used as a chiral compound or as a racemate—in which $R^3$ means $C_1$-$C_5$-alkyl, according to methods that are known to one skilled in the art to form alcohol (XI) and subsequent oxidation also according to methods of one skilled in the art to form aldehyde, or by reduced reduction, according to methods known to one skilled in the art, of ester X directly to the aldehyde.

Another subject of the invention is the process for the production of the compound of general formula X, which can be obtained by Friedel-Crafts alkylation of 5-fluoro-2,3-dihydrobenzofuran and then subjected to an enantiomer separation.

An alternative process for the production of the compounds of formulas IIa and IIb is performed as follows:

Isobutene is reacted with use of a Lewis acid catalyst, for example $TiCl_4$, $Ti(OR^3)_4$, $TiCl_2(OR^3)_2$, $TiBr_2(OR^3)_2$, $PdCl_4$, $Pd(OR^3)_4$, $PdCl_2(OR^3)_2$, $PdBr_2(OR^3)_2$, $ZnCl_2$, $ZnBr_2$, $AlCl_3$, $AlBr_3$, $AlEtCl_2$, $AlMe_2Cl$, Cu salts, e.g., $Cu(OTf)_2$, $CuCl_2$, $CuBr_2$, $Yb(OTf)_3$, chiral catalysts, such as, e.g., $(BINOL)_2TiCl_2$, $(BINAP)_2TiCl_2$, $(BINOL)_2PdCl_2$, $(BINAP)_2PdCl_2$, $(BINOL)_2TiBr_2$, $(BINAP)_2TiBr_2$, $(BINOL)_2PdBr_2$, $(BINAP)_2PdBr_2$, preferably $FeCl_3$, whereby $R^3$ means $C_1$-$C_5$-alkyl, with trifluoroethyl pyruvate to form 2-hydroxy-4-methyl-2-trifluoromethylpent-4-enoic acid ethyl ester XII. This reaction product is then reacted in an additional reaction step with 5-fluoro-2,3-dihydrobenzofuran to obtain a compound of formula (X). Reduction of the ester to alcohol (XI) and subsequent oxidation to aldehyde (III) or reduction of ester (X) to aldehyde (III) according to methods that are common to one skilled in the art develop with the aldehyde the direct precursors for the compounds of-general formulas IIa and IIb, which then can be obtained by reaction of aldehyde (III) with the corresponding quinolinamine or isoquinolinamine under conditions of reductive amination, as already described in the prior art. In the stage of ester (XII) or ester (X), an enantiomer separation can be performed. Also, alcohol (XI) is suitable for an enantiomer separation. A separate insertion of the chiral esters then leads to the enantiomer-pure compounds of general formulas IIa and IIb.

Another subject of the invention is a process for the production of compounds of general formula XII, in which $R^3$ means $C_1$-$C_5$-alkyl, by isobutene being reacted with use of a Lewis acid catalyst with trifluoroalkyl pyruvate and the reaction product being separated into the enantiomers.

As solvents for the reaction of isobutene with trifluoroethyl pyruvate, for example, $CH_2Cl_2$, tetrahydrofuran, dioxane, and diethyl ether are suitable.

A special aspect of the invention is the use of chiral Lewis acid catalysts for the process according to the invention.

One aspect of the invention is that the enantiomer separation is carried out in any stage of the synthesis using column chromatography on a chiral phase. The separation in the stage of the compound of formula IIa or IIb is a special aspect of the invention. The enantiomer separation in the stage of ester XII or X is another important aspect of the invention.

Another aspect of the invention is the separation of suitable racemic intermediate stages of the synthesis using chiral adjuvants. The racemic intermediate stages can be converted either with chiral adjuvants, e.g., bases into diastereomeric salts, or with chiral adjuvants into diastereomers, which then are subjected to a diastereomer separation. The chiral auxiliary reagent is then cleaved again and can be recovered.

Suitable chiral auxiliary reagents are known to one skilled in the art and can be found in, for example, the book "Chiral Auxiliaries and Ligands in Asymmetric Synthesis" by J. Seyden-Penne, Wiley Verlag, New York (1995).

Suitable intermediate stages for the separation of racemic intermediate stages are, for example:
  a) All precursors that have at least one alcohol function; in this connection, chiral acids are suitable as auxiliary reagents.
  b) Aldehyde precursors, such as, e.g., aldehyde (II), which is obtained after reduction of the ester to alcohol (XI) and subsequent oxidation to aldehyde (III) or reduction of ester (X) to aldehyde (III); other ester precursors in addition optionally also can be converted into the aldehydes for enantiomer separation. In this respect, auxiliary reagents are chiral diols that then form diastereomeric ketals, which can be separated and then cleaved again.
  c) All acids that optionally can be obtained from the ester precursors by cleavage of the existing ester function or by oxidation of compounds of lower oxidation stages according to methods that are known to one skilled in the art;
    Chiral alcohols or chiral amines can be used here as auxiliary reagents.
  d) All precursors that contain an ester function can be converted by re-esterification into diastereomeric esters and then can be treated as described under c).

If the compounds according to the invention are present as racemic mixtures, they can be separated into the pure, optically active forms according to the methods of racemate separation that are familiar to one skilled in the art. For example, the racemic mixtures can be separated into pure isomers by chromatography on an even optically active carrier material (CHIRALPAK AD®). Suitable precursors are compounds of general formulas III, IV, V, VI, VII, VIII, IX, X and XI.

It is also possible to esterify the free hydroxy group in a racemic compound of general formulas (IIa) and (IIb) or a suitable precursor with an optically active acid and to separate the diastereoisomeric esters that are obtained by fractionated crystallization or by chromatography and to saponify the separated esters in each case to the optically pure isomers. As optically active acid, for example, mandelic acid, camphorsulfonic acid or tartaric acid can be used. The auxiliary reagent optionally can be recovered as known to one skilled in the art.

Thus, a special subject of the invention is a process, as represented in one of the two above-described alternatives, which is characterized in that the diastereomer separation is performed in any suitable stage by esterification of an alcohol function with a chiral acid, separation of diastereomers and saponification with or without recovery of the chiral auxiliary reagent.

In the case that the compounds of general formulas (IIa) and (IIb) are present as salts, this can be, for example, in the form of hydrochloride, sulfate, nitrate, phosphate, pivalate, maleate, fumarate, tartrate, benzoate, mesylate, citrate or succinate.

Prodrugs are defined as compounds that are optionally changed only slightly compared to the claimed compounds, lie within or outside the range of equivalence of the claims, and are cleaved into the compounds that are claimed by metabolism in the organism or by contact with the organism. The prodrugs are subject to at least one biotransformatory step until the claimed compounds are released, which then exert their pharmacological effect.

The binding of the substances to the glucocorticoid receptor (GR) and other steroid hormone receptors (mineral corticoid receptor (MR), progesterone receptor (PR) and androgen receptor (AR)) is examined with the aid of recombinantly produced receptors. The binding experiments are with extracts from Sf9 cells, which had been infected with baculoviruses that contain the coding sequences for the respective steroid hormone receptor. In comparison to the reference substance [$^3$H]-dexamethasone, the substances show a high to very high affinity to GR.

Moreover, the quinolines and isoquinolines of formulas (IIa) and (IIb) that are described here show a high selectivity for the glucocorticoid receptor.

The GR-mediated inhibition of the transcription of cytokines, adhesion molecules, enzymes and other pro-inflammatory factors is considered to be an essential molecular mechanism for the anti-inflammatory action of glucocorticoids. This inhibition is produced by an interaction of the GR with other transcription factors, e.g., AP-1 and NF-kappa-B (for an overview, see Cato, A. C. B. and Wade, E., BioEssays 18, 371-378, 1996).

The compounds of general formulas (IIa) and (IIb) according to the invention inhibit the secretion of the cytokine IL-8, induced by lipopolysaccharide (LPS), in the human monocyte cell line THP-1. The concentration of the cytokines was determined in the supernatant by means of commercially available ELISA kits. (Efficiency of dexamethasone=100%); Example 1, $IC_{50}$=5.9 nmol (74% efficiency); Example 10, $IC_{50}$=21 nmol (86% efficiency); Example 11, $IC_{50}$=8.5 nmol (61% efficiency); prednisolone, $IC_{50}$=13 nmol (96% efficiency).

The anti-inflammatory actions of the compounds of general formulas (IIa) and (IIb) were tested in the animal experiment by tests in the croton-oil-induced inflammation in rats and/or mice (J. Exp. Med. (1995), 182, 99-108). To this end, croton oil in ethanolic solution was applied topically to the animals' ears. The test substances were administered locally at the same time. After 16-24 hours, the ear weight was measured as a measurement for the inflammatory edema, the peroxidase activity as a measurement for the invasions of granulocytes and the elastase activity as a measurement for the invasion of neutrophilic granulocytes. In this test, the compounds of general formulas (IIa) and (IIb) inhibit the three above-mentioned inflammation parameters after local administration.

One of the most frequent undesirable actions of a glucocorticoid therapy is the so-called "steroid diabetes" [cf. Hatz, H. J., Glucocorticoide: Immunologische Grundlagen, Pharmakologie und Therapierichtlinien [Glucocorticoids: Immunological Principles, Pharmacology and Therapy Guidelines], Wissenschaftliche Verlagsgesellschaft mbH, Stuttgart, 1998]. The reason for this is the stimulation of gluconeogenesis in the liver by induction of the enzymes that are responsible for this and by free amino acids that are produced from the degradation of proteins (catabolic action of glucocorticoids). A key enzyme of the catabolic metabolism in the liver is the tyrosine aminotransferase (TAT). The activity of this enzyme can be determined photometrically from cell cultures of treated rat hepatoma cells. The cells are treated for 24 hours with the test substances, and then the TAT activity is measured. The compounds of general formulas (IIa) and (IIb) induce the trysoinaminotransferase in this test to a slight extent (efficiency of dexamethasone=100%); Example 1, $EC_{50}$=3.7 nmol (93% efficiency); Example 10, $EC_{50}$=10 nmol (92% efficiency); Example 11, $EC_{50}$=4.0 nmol (86% efficiency); prednisolone, $EC_{50}$=2.6 nmol (103% efficiency).

Another undesirable action that occurs especially after local therapy is the induction of a skin atrophy, which leads to the skin's loss of thickness, elasticity, and ultimately the mechanical resistance of the skin. The potential of a substance to induce skin atrophy can be determined in rats. The animals are treated for 18 days daily and locally in equieffective dosages with the test substances. By means of a skin fold thickness measurement, the reduction of the skin thickness over the treatment time can be tracked.

In comparison to clobetasol propionate, which, at a concentration of 0.01% (maximum anti-inflammatory action is achieved), results in a 65% reduction of the skin thickness, only a 41% reduction can be determined in Example 1 at a concentration of 0.1% (maximum anti-inflammatory action is achieved).

This advantage can also be seen relative to the substances from the application WO 03/082827; for example, the eutomer of Example 36, already at a concentration of 0.06% (maximum anti-inflammatory action), induces a 60% reduction in skin thickness.

Based on their anti-inflammatory action and, in addition, anti-allergic, immunosuppressive and anti-proliferative action, the compounds of general formulas (IIa) and (IIb) according to the invention can be used as medications for treatment or prophylaxis of the following pathologic conditions in mammals and humans; in particular for the local administration:

In this case, the term "DISEASE" stands for the following indications:
(i) Lung diseases that are accompanied by inflammatory, allergic and/or proliferative processes:
   Chronic, obstructive lung diseases of any origin, primarily bronchial asthma
   Bronchitis of different origins
   Adult respiratory distress syndrome (ARDS), acute respiratory distress syndrome
   Bronchiectases
   All forms of restrictive lung diseases, primarily allergic alveolitis,
   All forms of pulmonary edema, primarily toxic pulmonary edema; e.g., radiogenic pneumonitis
   Sarcoidoses and granulomatoses, especially Boeck's disease
(ii) Rheumatic diseases/autoimmune diseases/joint diseases that are accompanied by inflammatory, allergic and/or proliferative processes:
   All forms of rheumatic diseases, especially rheumatoid arthritis, acute rheumatic fever, polymyalgia rheumatica, Behcet's disease
   Reactive arthritis
   Inflammatory soft-tissue diseases of other origins
   Arthritic symptoms in the case of degenerative joint diseases (arthroses)
   Traumatic arthritides
   Vitiligo
   Collagenoses of any origin, e.g., systemic lupus erythematodes, sclerodermia, polymyositis, dermatomyositis, Sjögren's syndrome, Still's syndrome, Felty's syndrome
   Sarcoidoses and granulomatoses
   Soft-tissue rheumatism
(iii) Allergies or pseudoallergic diseases that are accompanied by inflammatory and/or proliferative processes:
   All forms of allergic reactions, e.g., Quincke's edema, hay fever, insect bites, allergic reactions to pharmaceutical agents, blood derivatives, contrast media, etc., anaphylactic shock, urticaria, allergic and irritative contact dermatitis, allergic vascular diseases
   Allergic vasculitis
(iv) Vascular inflammations (vasculitides)
   Panarteritis nodosa, temporal arteritis, erythema nodosum
   Polyarteris nodosa
   Wegner's granulomatosis
   Giant-cell arteritis
(v) Dermatological diseases that are accompanied by inflammatory, allergic and/or proliferative processes:
   Atopic dermatitis (primarily in children)
   All forms of eczema, such as, e.g., atopic eczema (primarily in children)
   Rashes of any origin or dermatoses
   Psoriasis and parapsoriasis groups
   Pityriasis rubra pilaris
   Erythematous diseases, triggered by different noxae, e.g., radiation, chemicals, burns, etc.
   Bullous dermatoses, such as, e.g., autoimmune pemphigus vulgaris, bullous pemphigoid
   Diseases of the lichenoid group,
   Pruritis (e.g., of allergic origin)
   Seborrheal eczema
   Rosacea group
   Erythema exudativum multiforme
   Balanitis
   Vulvitis
   Manifestation of vascular diseases
   Hair loss such as alopecia areata
   Cutaneous lymphoma
(vi) Kidney diseases that are accompanied by inflammatory, allergic and/or proliferative processes:
   Nephrotic syndrome
   All nephritides, e.g., glomerulonephritis
(vii) Liver diseases that are accompanied by inflammatory, allergic and/or proliferative processes:
   Acute liver cell decomposition
   Acute hepatitis of different origins, e.g., viral, toxic, pharmaceutical agent-induced
   Chronic aggressive hepatitis and/or chronic intermittent hepatitis
(viii) Gastrointestinal diseases that are accompanied by inflammatory, allergic and/or proliferative processes:
   Regional enteritis (Crohn's disease)
   Colitis ulcerosa
   Gastritis
   Reflux esophagitis
   Ulcerative colitis of other origins, e.g., native sprue
(ix) Proctologic diseases that are accompanied by inflammatory, allergic and/or proliferative processes:
   Anal eczema
   Fissures
   Hemorrhoids
   Idiopathic proctitis (x) Eye diseases that are accompanied by inflammatory, allergic and/or proliferative processes:
Allergic keratitis, uveitis, iritis
Conjunctivitis
Blepharitis
Optic neuritis
Chorioiditis
Sympathetic ophthalmia
(xi) Diseases of the ear-nose-throat area that are accompanied by inflammatory, allergic and/or proliferative processes:
Allergic rhinitis, hay fever
Otitis externa, e.g., caused by contact dermatitis, infection, etc.
Otitis media
(xii) Neurological diseases that are accompanied by inflammatory, allergic and/or proliferative processes:
Cerebral edema, primarily tumor-induced cerebral edema
Multiple sclerosis
Acute encephalomyelitis
Meningitis
Various forms of convulsions, e.g., infantile nodding spasms
Acute spinal cord injury
Stroke
(xiii) Blood diseases that are accompanied by inflammatory, allergic and/or proliferative processes, such as, e.g.: M. Hodgkins or Non-Hodgkins lymphomas, thrombocythemias, erythrocytoses
Acquired hemolytic anemia
Idiopathic thrombocytopenia
(xiv) Tumor diseases that are accompanied by inflammatory, allergic and/or proliferative processes, such as, e.g.: carcinomas or sarcomas
Acute lymphatic leukemia
Malignant lymphoma
Lymphogranulomatoses
Lymphosarcoma
Extensive metastases, mainly in breast, bronchial and prostate cancers
(xv) Endocrine diseases that are accompanied by inflammatory, allergic and/or proliferative processes, such as, e.g.:
Endocrine orbitopathy
Thyreotoxic crisis
De Quervain's thyroiditis
Hashimoto's thyroiditis
Basedow's disease
Granulomatous thyroiditis
Lymphadenoid goitre
(xvi) Organ and tissue transplants, graft-versus-host disease
(xvii) Severe shock conditions, e.g., anaphylactic shock, systemic inflammatory response syndrome (SIRS)
(xviii) Substitution therapy in:
Innate primary suprarenal insufficiency, e.g., congenital adrenogenital syndrome
Acquired primary suprarenal insufficiency, e.g., Addison's disease, autoimmune adrenalitis, meta-infective tumors, metastases, etc.
Innate secondary suprarenal insufficiency, e.g., congenital hypopituitarism
Acquired secondary suprarenal insufficiency, e.g., meta-infective tumors, etc.
(xix) Vomiting that is accompanied by inflammatory, allergic and/or proliferative processes:
e.g., in combination with a 5-HT3 antagonist in cytostatic-agent-induced vomiting
(xx) Pains of inflammatory origins, e.g., lumbago
(xxi) Other different stages of disease including diabetes type I (insulin-dependent diabetes), osteoarthritis, Guillain-Barré syndrome, restenoses after percutaneous transluminal angioplasty, Alzheimer's disease, acute and chronic pain, arteriosclerosis, reperfusion injury, congestive heart failure, myocardial infarction, thermal injury, multiple organ injury secondary to trauma, acute purulent meningitis, necrotizing enterocolitis and syndromes associated with hemodialysis, leukopheresis, and granulocyte transfusion.

The local administration of the compounds or mixture thereof according to the invention for treating the diseases that are cited under Items (i), (ii), (iii), (v), (viii), (ix), (x), (xi), (xv), (xx), and (xxi) is preferred.

The invention also relates to combination therapies or combined compositions, in which a glucocorticoid receptor (GR) agonist of formula (I) or a pharmaceutically acceptable salt thereof, or a pharmaceutical composition that contains a GR agonist of formula (I) or a pharmaceutically acceptable salt thereof, is administered either simultaneously (optionally in the same composition) or in succession together with one or more pharmaceutical agents for treating one of the above-mentioned pathologic conditions. For example, for treatment of rheumatoid arthritis, osteoarthritis, COPD (chronic obstructive lung disease), asthma or allergic rhinitis, a GR agonist of this invention can be combined with one or more pharmaceutical agents for treating such a condition. When such a combination of a GR agonist of formula (I) or a pharmaceutically acceptable salt thereof is administered by inhalation, the pharmaceutical agent that is to be combined can be selected from the following list:

A PDE4 inhibitor including an inhibitor of the PDE4D isoform,

A selective $\beta_2$.adrenoceptor agonist, such as, for example, metaproterenol, isoproterenol, isoprenaline, albuterol, salbutamol, formoterol, salmeterol, terbutaline, orciprenaline, bitolterol mesylate, pirbuterol or indacaterol;

A muscarine receptor antagonist (for example, an M1, M2 or M3 antagonist, such as, for example, a more selective M3 antagonist), such as, for example, ipratropium bromide, tiotropium bromide, oxitropium bromide, pirenzepine or telenzepine;

A modulator of the chemokine receptor function (such as, for example, a CCR1 receptor antagonist); or An inhibitor of the p38 kinase function.

Moreover, the compounds of general formulas (IIa) and (IIb) according to the invention can be used for treatment and prophylaxis of additional pathologic conditions that are not mentioned above, for which synthetic glucocorticoids are now used (see in this respect Hatz, H. J., Glucocorticoide: Immunologische Grundlagen, Pharmakologie und Therapierichtlinien, Wissenschaftliche Verlagsgesellschaft mbH, Stuttgart, 1998).

All previously mentioned indications (i) to (xx) are described in more detail in Hatz, H. J., Glucocorticoide: Immunologische Grundlagen, Pharmakologie und Therapierichtlinien, Wissenschaftliche Verlagsgesellschaft mbH, Stuttgart, 1998.

For the therapeutic actions in the above-mentioned pathologic conditions, the suitable dose varies and depends on, for example, the active strength of the compound of general formulas (IIa) and (IIb), the host, the type of administration, and the type and severity of the conditions that are to be treated, as well as the use as a prophylactic agent or therapeutic agent.

The invention relates to the use of the compounds according to the invention for the production of a pharmaceutical agent.

In addition, the invention provides:
(i) The use of one of the compounds of formulas (IIa) and (IIb) according to the invention or mixture thereof for the production of a medication for treating a DISEASE;
(ii) A process and a method for treating a DISEASE, said process comprises an administration of an amount of the compound according to the invention whereby the amount suppresses the disease and whereby the amount of the compound is given to a patient who requires such a medication;
(iii) A pharmaceutical composition for treating a DISEASE, said treatment comprises one of the compounds according to the invention or mixture thereof and at least one pharmaceutical adjuvant and/or vehicle.

In particular, the use of the compounds according to the invention for treatment of inflammatory diseases is a subject of the invention.

In general, satisfactory results can be expected in animals when the daily doses comprise a range of 1 µg to 100,000 µg of the compound according to the invention per kg of body weight. In the case of larger mammals, for example the human, a recommended daily dose lies in the range of 1 µg to 100,000 µg per kg of body weight. Preferred is a dose of 10 to 30,000 µg per kg of body weight, and more preferred is a dose of 10 to 10,000 µg per kg of body weight. For example, this dose is suitably administered several times daily.

The formulation of the pharmaceutical preparations based on the new compounds is carried out in a way that is known in the art by the active ingredient being processed with the vehicles, fillers, substances that influence decomposition, binding agents, moisturizers, lubricants, absorbents, diluents, flavoring correctives, coloring agents, etc., that are commonly used in galenicals and converted into the desired form of administration. In this case, reference is made to Remington's Pharmaceutical Science, 15$^{th}$ Edition, Mack Publishing Company, East Pennsylvania (1980). Additives that are suitable for local administration are especially preferred.

For oral administration, especially tablets, coated tablets, capsules, pills, powders, granulates, lozenges, suspensions, emulsions or solutions are suitable.

For parenteral administration, injection preparations are possible.

For intra-articular injection, correspondingly prepared crystal suspensions can be used.

For intramuscular injection, aqueous and oily injection solutions or suspensions and corresponding depot preparations can be used.

For rectal administration, the new compounds can be used in the form of suppositories, capsules, solutions (e.g., in the form of enemas) and ointments both for systemic and for local treatment.

For pulmonary administration of the new compounds, the latter can be used in the form of aerosols and inhalants.

For local application to eyes, outer ear channels, middle ears, nasal cavities, and paranasal sinuses, the new compounds can be used as drops, ointments and tinctures in corresponding pharmaceutical preparations.

For topical application, formulations in gels, ointments, fatty ointments, creams, pastes, powders, emulsions, solutions and suspensions are possible. The dosage of the compounds of general formulas (IIa) and (IIb) should be 0.01%-20% in these preparations to achieve a sufficient pharmacological action.

The invention also comprises the compounds of general formulas (IIa) and (IIb) according to the invention as therapeutic active ingredients. In addition, the compounds of general formulas (IIa) and (IIb) according to the invention are part of the invention as therapeutic active ingredients together with pharmaceutically compatible and acceptable adjuvants and vehicles.

The invention also comprises a pharmaceutical composition that contains one of the pharmaceutically active compounds according to the invention or mixture thereof or pharmaceutically compatible salt thereof and a pharmaceutically compatible salt or pharmaceutically compatible adjuvants and vehicles.

The examples below are used for a more detailed explanation of the invention without intending that it be limited thereto. The syntheses of important precursors, which are not disclosed within the scope of the experiments, are already prior art and can be derived from, for example, WO 98/54159 and WO 02/10143, WO 03/082280 or WO 03/082827.

Experiments

EXAMPLE 1

5-[4-(5-Fluoro-2, 3-dihydrobenzofuran-7-yl)-2-hydroxy-4-methyl-2-trifluoromethyl-pentylamino]-2-methylquinoline 4-(5-Fluoro-2-hydroxyphenyl)-2-hydroxy-4-methyl-2-trifluoromethyl-valeric acid ethyl ester A solution of 4-(5-fluoro-2-methoxyphenyl)-2-hydroxy-4-methyl-2-trifluoromethyl-valeric acid ethyl ester (WO 00/32584) (10.83 g, 30.74 mmol) in dichloromethane (200 ml) is mixed with 1 M boron tribromide-chloroform solution (60 ml) while being cooled in an ice bath, and it is stirred for 3 hours at 2-4° C. The batch is poured onto ice and saturated NaHCO$_3$ solution, and it is stirred for 30 minutes while being cooled with ice. The organic phase is separated, and the aqueous phase is extracted twice more with dichloromethane. The combined, organic extracts are washed with saturated NaCl solution, dried (Na$_2$SO$_4$) and concentrated by evaporation in a vacuum. Column chromatography of the residue (silica gel) with hexane-ethyl acetate yields 5.36 g of product. Extraction of the aqueous phase with ethyl acetate yields 4.0 g of product again.

$^1$H-NMR (300 MHz, CDCl$_3$); δ=1.22 (t, 3H), 1.41 (s, 3H), 1.47 (s, 3H), 2.52 (d, 1H), 2.87 (d, 1H), 3.55 (br, 1H), 3.76 (dq, 1H), 4.11 (dq, 1H), 5.01 (s, 1H), 6.59 (dd, 1H), 6.77 (ddd, 1H), 6.90 (dd, 1H).

4-(2-Allyloxy-5fluorophenyl)-2-hydroxy-4-methyl-2-trifluoromethyl-valeric acid ethyl ester Potassium carbonate (4.15 g, 30 mmol) and allyl bromide (2.16 ml, 25 mmol) are added to a solution of 4-(5-fluoro-2-hydroxyphenyl)-2-hydroxy-4-methyl-2-trifluoromethyl-valeric acid ethyl ester (5.36 g, 15.84 mmol) in DMF (50 ml) while being cooled with ice. After 2 hours at 2° C. and after 2 hours at room temperature, the batch is poured into ice water and extracted with hexane-ether 2:1. The combined organic extracts are dried (Na$_2$SO$_4$) and concentrated by evaporation in a vacuum. Column chromatography on silica gel with hexane-ethyl acetate yields 5.7 g of the product.

$^1$H-NMR (300 MHz, CDCl$_3$); δ=1.18 (t, 3H), 1.39 (s, 3H), 1.45 (s, 3H), 2.54 (d, 1H), 2.91 (d, 1H), 3.48 (br, 1H), 3.65

(dq, 1H), 4.09 (dq, 1H), 4.55 (dt, 2H), 5.31 (dq, 1H), 5.45 (dq, 1H), 6.09 (ddt, 1H), 6.76 (dd, 1H), 6.84 (ddd, 1H), 6.91 (dd, 1H).

4-(3-Allyl-5fluoro-2-hydroxyphenyl)-2-hydroxy-4-methyl-2-trifluoromethyl-valeric acid ethyl ester 4-(2-Allyloxy-5-fluorophenyl)-2-hydroxy-4-methyl-2-trifluoromethyl-valeric acid ethyl ester (5.65 g, 14.93 mmol) is heated in the microwave for 10 minutes to 230° C. The reaction mixture is purified by column chromatography on silica gel with hexane-ethyl acetate. 3.31 g of product is obtained.

$^1$H-NMR (300 MHz, CDCl$_3$); δ=1.23 (t, 3H), 1.40 (s, 3H), 1.45 (s, 3H), 2.60 (d, 1H), 2.78 (d, 1H), 3.37 (d, 2H), 3.49 (br, 1H), 3.83 (dq, 1H), 4.14 (dq, 1H), 5.09 (br, 1H), 5.23 (dq, 1H), 5.26 (dq, 1H), 5.99 (ddt, 1H), 6.72 (dd, 1H), 6.83 (dd, 1H).

4-(5-Fluoro-2-hydroxy-3-(2-hydroxyethyl)phenyl)-2-hydroxy-4-methyl-2-trifuoromethyl-valeric acid ethyl ester 4-(3-Allyl-5-fluoro-2-hydroxyphenyl)-2-hydroxy-4-methyl-2-trifluoromethyl-valeric acid ethyl ester (4.9 g, 12.95 mmol) in acetone (214 ml) and water (32 ml) are mixed with N-methylmorpholine oxide-hydrate (1.75 g, 12.95 mmol) and 0.4 ml of osmium tetroxide solution (2.5% by weight in tert-butanol) while being cooled with ice. After 30 minutes at 2° C. and 16 hours at room temperature, the batch is mixed with another 0.3 ml of osmium tetroxide solution and stirred for 3 days at room temperature. For working-up, acetone is distilled off in a rotary evaporator, the residue is taken up in ethyl acetate (200 ml) and water (150 ml), and the phases are separated. The aqueous phase is extracted twice more with ethyl acetate, the combined ethyl acetate extracts are washed with saturated NaCl solution, dried (Na$_2$SO$_4$) and concentrated by evaporation. Column chromatography on silica gel with hexane-ethyl acetate yields 5.27 g of 4-(3-(2,3-dihydroxypropyl)-5-fluoro-2-hydroxyphenyl)-2-hydroxy-4-methyl-2-trifluoromethyl-valeric acid ethyl ester. The latter (5.2 g, 12.6 mmol) is stirred with sodium periodate (5.39, 25.2 mmol) in THF (75 ml) and water (12.5 ml) for 24 hours under nitrogen. The batch is concentrated by evaporation, and the aqueous residue is extracted three times with ethyl acetate. The combined organic phases are washed with saturated NaCl solution, dried (Na$_2$SO$_4$) and concentrated by evaporation in a vacuum. Column chromatography on silica gel with hexane-ethyl acetate yields 4.3 g of 4-(5-fluoro-2-hydroxy-2,3-dihydrobenzofuran-7-yl)-2-hydroxy-4-methyl-2-trifluoromethyl-valeric acid ethyl ester. 4.1 g (10.78 mmol) thereof in methanol (150 ml) is dissolved, the solution is mixed in portions with sodium borohydride (586 mg, 15 mmol), and it is stirred for 30 minutes at room temperature. A pH of 7.5 is set with acetic acid, and the reaction mixture is concentrated by evaporation. The residue is taken up in ethyl acetate (200 ml) and saturated NaHCO$_3$ solution (75 ml), the phases are separated, the organic phase is washed with saturated NaCl solution, dried (Na$_2$SO$_4$) and concentrated by evaporation in a vacuum, whereby 4.01 g of product accumulates.

$^1$H-NMR (300 MHz, CDCl$_3$); δ=1.23 (t, 3H), 1.40 (s, 3H), 1.47 (s, 3H), 2.59 (d, 1H), 2.76-2.92 (m, 2H), 2.91 (d, 1H), 3.85 (dq, 1H), 3.98 (m, 2H), 4.05 (dq, 1H), 6.67 (dd, 1H), 6.81 (dd, 1H).

4-(5-Fluoro-2,3-dihydrobenzofuran-7-yl)-2-hydroxy-4-methyl-2-trifluoromethyl-valeric acid ethyl ester 4-(5-Fluoro-2-hydroxy-3-(2-hydroxyethyl)phenyl)-2-hydroxy-4-methyl-2-trifluoromethyl-valeric acid ethyl ester (3.90 g, 10.2 mmol) is dissolved with triphenylphosphine (3.14 g, 12 mmol) and triethylamine (2.1 ml, 15 mmol) in acetonitrile (150 ml), mixed with carbon tetrachloride (2 ml) and stirred for 3 days in a nitrogen atmosphere at room temperature. The solvent is distilled off in a rotary evaporator, and the residue is taken up in ethyl acetate (150 ml) and water (75 ml). The ethyl acetate phase is separated, washed with saturated NaCl solution, dried (Na$_2$SO$_4$) and concentrated by evaporation in a vacuum. Column chromatography on silica gel with hexane-ethyl acetate yields 3.31 g of the product.

$^1$H-NMR (300 MHz, CDCl$_3$); δ=1.21 (t, 3H), 1.35 (s, 3H), 1.40 (s, 3H), 2.43 (d, 1H), 2.74 (d, 1H), 3.15 (m, 2H), 3.56 (br, 1H), 3.73 (dq, 1H), 4.13 (dq, 1H), 4.58 (t, 2H), 6.68 (dd, 1H), 6.77 (dm, 1H).

4-(5-Fluoro-2, 3-dihydrobenzofuran-7-yl)-4-methyl-2-trifluoromethyl-1,2-pentadiol A solution of 4-(5-fluoro-2,3-dihydrobenzofuran-7-yl)-2-hydroxy-4-methyl-2-trifluoromethyl-valeric acid ethyl ester (3.2 g, 8.78 mmol) in ether (150 ml) is mixed with lithium aluminum hydride (683 mg, 18 mmol) while being cooled with ice, and it is stirred for 1 hour at 2° C. and for 6 hours at room temperature. The batch is cooled to 3° C., saturated HaHCO$_3$ solution (1.5 ml) is added in drops thereto, and it is stirred for 30 minutes at 3° C. and for 16 hours at room temperature. The colorless precipitate is suctioned off and washed with ether. The combined filtrates are concentrated by evaporation and purified by column chromatography on silica gel with hexane-ethyl acetate. 2.65 g of the product accumulates as colorless, crystalline solid.

$^1$H-NMR (300 MHz, CDCl$_3$); δ=1.39 (s, 3H), 1.47 (s, 3H), 2.21 (d, 1H), 2.46 (d, 1H), 2.89 (br, 1H), 3.17 (t, 2H), 3.41 (dm, 1H), 3.49 (d, 1H), 4.57 (t, 2H), 6.80 (d, 2H).

4-(5-Fluoro-2,3-dihydrobenzofuran-7-yl)-2-hydroxy-4-methyl-2-trifluoromethyl-pentanal Pyridine-sulfur trioxide complex (3.82 g, 24 mmol) is added under nitrogen atmosphere to a solution of 4-(5-fluoro-2,3-dihydrobenzofuran-7-yl)-4-methyl-2-trifluoromethyl-1, 2-pentadiol (2.61 g, 8.1 mmol), dimethyl sulfoxide (28.6 ml) and triethylamine (5.6 ml, 40 mmol) in dichloromethane (85 ml). The batch is stirred for 3 hours at room temperature, mixed with saturated NH$_4$Cl solution (50 ml), stirred for 30 minutes at room temperature and diluted with ether (250 ml). The phases are separated, and the aqueous phase is extracted with ether. The combined organic phases are washed with saturated NaCl solution, dried (Na$_2$SO$_4$) and concentrated by evaporation in a vacuum. Column chromatography of the residue on silica gel with hexane-ethyl acetate yields 2.19 g of the product.

$^1$H-NMR (300 MHz, CDCl$_3$); δ=1.35 (s, 3H), 1.42 (s, 3H), 2.20 (d, 1H), 3.17 (t, 2H), 3.28 (d, 1H), 3.62 (s, 1H), 4.59 (m, 2H), 6.63 (dd, 1H), 6.81 (dm, 1H), 9.08 (s, 1H).

2-Methyl-5-nitroquinoline

2-Methylquinoline (108.3 ml, 0.80 mol) is added in drops to 65% nitric acid (61 ml, 0.88 mol) at an internal temperature of 0-10° C. (dry ice cooling) within 45 minutes. After 1 hour, the precipitated nitrate is suctioned off and introduced in portions at an internal temperature of 0-6° C. in concentrated sulfuric acid (240 ml). After 30 minutes, potassium nitrate (6 g, 60 mmol) is added thereto, and it is stirred for 16 hours at room temperature. The batch is slowly poured onto ice/water, and a pH of 1.5 is set with 40% NaOH (~500 ml). The precipitate is suctioned off, the filtrate is made alkaline with 25% ammonia water (pH 10) and filtered. The filter residue is dissolved in hot methanol (500 ml). During cooling, the 8-nitro-isomer crystallizes out. The mother liquor is concentrated by evaporation and purified by column chromatography on silica gel with hexane-ethyl acetate, whereby 53 g of the 2-methyl-5-nitroquinoline accumulates.

$^1$H-NMR (300 MHz, CDCl$_3$); δ=2.79 (s, 3H), 7.52 (d, 1H), 7.76 (d, 1H), 8.31 (d, 1H), 8.32 (d, 1H), 8.88 (d, 1H).

5-Amino-2-methylquinoline

2-Methyl-5-nitroquinoline (25 g, 132.85 mmol) and palladium on carbon (2.5 g) in 8 ml of glacial acetic acid are stirred for 5½ hours in a hydrogen atmosphere at normal pressure. The catalyst is suctioned off and washed with ethyl acetate. The combined filtrates are concentrated by evaporation. Column chromatography of the residue on silica gel with dichloromethane-acetone yields 10.6 g of the product.

$^1$H-NMR (300 MHz, CDCl$_3$); δ=2.72 (s, 3H), 4.15 (br, 2H), 6.76 (dd, 1H), 7.23 (d, 1H), 7.43-7.50 (m, 2H), 8.06 (d, 1H).

5-[4-(5-Fluoro-2, 3-dihydrobenzofuran-7-yl)-2-hydroxy-4-methyl-2-trifluoromethyl-pentylidenamino]-2-methylquinoline A mixture that consists of 4-(5-fluoro-2,3-dihydrobenzofuran-7-yl)-2-hydroxy-4-methyl-2-trifluoromethyl-pentanal (320 mg, 1 mmol) and 5-amino-2-methylquinoline (190 mg, 1.2 mmol) in acetic acid (2 ml) is stirred for 16 hours at room temperature, diluted with 10 ml of toluene and heated for 4 hours in a water separator. The batch is concentrated by evaporation, whereby the acetic acid is removed azeotropically with toluene. The residue is purified by column chromatography on silica gel with hexane-ethyl acetate: 274 mg of the product accumulates as colorless crystals.

$^1$H-NMR (300 MHz, CDCl$_3$); δ=1.34 (s, 3H), 1.54 (s, 3H), 2.27 (d, 1H), 2.66 (m, 1H), 2.76 (s, 3H), 2.94 (m, 1H), 3.29 (d, 1H), 4.47 (m, 2H), 4.85 (s, 1H), 6.28 (dm, 1H), 6.51 (d, 1H), 6.61 (dd, 1H), 7.33 (d, 1H), 7.51 (t, 1H), 7.63 (s, 1H), 7.90 (d, 1H), 8.18 (d, 1H).

5-[4-(5-Fluoro-2, 3-dihydrobenzofuran-7-yl)-2-hydroxy-4-methyl-2-trifluoromethyl-pentylamino]-2-methylquinoline 5-[4-(5-Fluoro-2,3-dihydrobenzofuran-7-yl)-2-hydroxy-4-methyl-2-trifluoromethyl-pentylidenamino]-2-methylquinoline (266 mg, 0.58 mmol) and sodium bicarbonate (250 mg) in methanol (15 ml) are stirred for 15 minutes at room temperature. Sodium borohydride (152 mg, 4 mmol) is added thereto in 4 portions over 24 hours. After the reaction is completed (TLC monitoring), the batch is mixed with saturated NaHCO$_3$ solution (10 ml) and concentrated by evaporation. The residue is taken up in ethyl acetate (30 ml) and water (20 ml), and the phases are separated. The aqueous phase is extracted with ethyl acetate. The combined organic phases are dried (Na$_2$SO$_4$) and concentrated by evaporation. Column chromatography on silica gel with hexane-ethyl acetate yields 200 mg of the product.

$^1$H-NMR (300 MHz, CDCl$_3$); δ=1.43 (s, 3H), 1.54 (s, 3H), 2.29 (d, 1H), 2.68 (d, 1H), 2.71 (s, 3H), 2.92-3.19 (m, 3H), 3.34 (dd, 1H), 4.26 (br, 1H), 4.52 (m, 2H), 6.09 (dm, 1H), 6.81 (dm, 1H), 6.87 (dm, 1H), 7.20 (d, 1H), 7.39-7.47 (m, 2H), 7.89 (d, 1H).

The enantiomers are separated by means of chiral HPLC with use of the column type Chiralpak AD 20µ and the eluant hexane (0.1% diethylamine)—ethanol in (+)- and (−)-isomer. The (−)-enantiomer ([α]$_D$(THF) −43.2°, c=1.45) is eluted before the (+)-enantiomer (([α]$_D$(THF) +42.8°, c=1.53).

EXAMPLE 2

5-[4-(5-Fluoro-2,3-dihydrobenzofuran-7-yl)-2-hydroxy-4-methyl-2-trifluoromethyl-pentylamino]-1-methylisoquinoline Analogously to Example 1, 4-(5-fluoro-2,3-dihydrobenzofuran-7-yl)-2-hydroxy-4-methyl-2-trifluoromethyl-pentanal is converted with 5-amino-1-methylisoquinoline into 5-[4-(5-fluoro-2,3-dihydrobenzofuran-7-yl)-2-hydroxy-4-methyl-2-trifluoromethyl-pentylidenamino]-1-methylisoquinoline, which is reduced with sodium borohydride to the product.

$^1$H-NMR (300 MHz, CDCl$_3$); δ=1.43 (s, 3H), 1.55 (s, 3H), 2.29 (d, 1H), 2.69 (d, 1H), 2.90 (s, 3H), 2.90-3.20 (m, 4H), 3.33 (br, 1H), 4.35 (br, 1H), 4.53 (m, 2H), 6.26 (d, 1H), 6.80 (dm, 1H), 6.88 (dm, 1H), 7.29 (t, 1H), 7.35 (d, 1H), 7.48 (d, 2H), 8.32 (d, 1H).

Separation of the enantiomers by means of chiral HPLC (column: Chiralpak AD 20µ, eluant: hexane-ethanol) first yields the (+)-enantiomer ([α]$_D$(MeOH) +29.8°, c=0.54) and then the (−)-enantiomer ([α]$_D$(MeOH) −29.4°, c=0.55).

EXAMPLE 3

5-[4-(5-Fluoro-2,3-dihydrobenzofuran-7-yl)-2-hydroxy-4-methyl-2-trifluoromethyl-pentylamino]isoquinol-1(2H)-one Analogously to Example 1, 4-(5-fluoro-2,3-dihydrobenzofuran-7-yl)-2-hydroxy-4-methyl-2-trifluoromethyl-pentanal is converted with 5-aminoisoquinol-2(1H)-one into 5-[4-(5-fluoro-2,3-dihydrobenzofuran-7-yl)-2-hydroxy-4-methyl-2-trifluoromethyl-pentylidenamino]isoquinol-1(2H)-one, which is reduced with sodium borohydride to the product.

$^1$H-NMR (300 MHz, [D]$_6$-DMSO); δ=1.33 (s, 3H), 1.52 (s, 3H), 1.98 (d, 1H), 2.78 (d, 1H), 2.84-3.10 (m, 4H), 4.49 (t, 1H), 4.80 (t, 1H), 6.03 (s, 1H), 6.21 (d, 1H), 6.41 (d, 1H), 6.80-6.87 (m, 2H), 7.12-7.17 (m, 2H), 7.47 (d, 1H), 11.21 (br. d, 1H).

Separation of the enantiomers by means of chiral HPLC (column: Chiralpak AS 20 µ, eluant: hexane-ethanol) first yields the (+)-enantiomer ([α]$_D$(MeOH) +29.9°, c=0.92) and then the (−)-enantiomer ([α]$_D$(MeOH) −28.4°, c=0.94).

EXAMPLE 4

5-[4-(5-Fluoro-2,3-dihydrobenzofuran-7-yl)-2-hydroxy-4-methyl-2-trifluoromethyl-pentylamino]-2,6-dimethylquinoline Analogously to Example 1, 4-(5-fluoro-2,3-dihydrobenzofuran-7-yl)-2-hydroxy-4-methyl-2-trifluoromethyl-pentanal is converted with 5-amino-2,6-dimethylquinoline into 5-[4-(5-fluoro-2,3-dihydrobenzofuran-7-yl)-2-hydroxy-4-methyl-2-trifluoromethyl-pentylidenamino]-2,6-dimethylquinoline, which is reduced with sodium cyanoborohydride to the product.

$^1$H-NMR (300 MHz, CDCl$_3$); δ=1.34 (s, 3H), 1.57 (s, 3H), 2.22 (d, 1H), 2.31 (s, 3H), 2.45 (d, 1H), 2.66-2.76 (m, 1H), 2.74 (s, 3H), 2.83-3.00 (m, 2H), 3.10 (d, 1H), 3.52 (br. 1H), 4.20 (q, 1H), 4.29 (s, 1H), 4.38 (q, 1H), 6.55 (d, 1H), 6.77 (dm, 1H), 7.22 (d, 1H), 7.42 (d, 1H), 7.68 (d, 1H), 7.94 (d, 1H).

Separation of the enantiomers by means of chiral HPLC (column: Chiralcel OJ 5 µ, eluant: hexane-ethanol) first yields the (+)-enantiomer ([α]$_D$(MeOH) +55.8°, c=0.94) and then the (−)-enantiomer ([α]$_D$(MeOH) −52.1°, c=0.99).

EXAMPLE 5

5-[4-(5-Fluoro-2,3-dihydrobenzofuran-7-yl)-2-hydroxy-4-methyl-2-trifluoromethyl-pentylamino]-6-chloro-2-methylquinoline Analogously to Example 1, 4-(5-fluoro-2,3-dihydrobenzofuran-7-yl)-2-hydroxy-4-methyl-2-trifluoromethyl-pentanal is converted with 5-amino-6-chloro-2-methylquinoline into 5-[4-(5-fluoro-2,3-dihydrobenzofuran-7-yl)-2-hydroxy-4-methyl-2-trifluoromethyl-pentylidenamino]-6-chloro-2-methylquinoline, which is reduced with sodium cyanoborohydride to the product.

$^1$H-NMR (300 MHz, CDCl$_3$); δ=1.34 (s, 3H), 1.57 (s, 3H), 2.22 (d, 1H), 2.53 (d, 1H), 2.75 (s, 3H), 2.72-2.83 (m, 1H), 2.89-3.02 (m, 2H), 3.16 (dd, 1H), 4.04 (s, 1H), 4.30 (q, 1H), 4.42 (q, 1H), 6.51 (dm, 1H), 6.73 (dd, 1H), 7.26 (d, 1H), 7.55 (d, 1H), 7.66 (d, 1H), 7.96 (d, 1H).

Separation of the enantiomers by means of chiral HPLC (column: Chiralcel OJ 20 µ, eluant: hexane-ethanol) first yields the (+)-enantiomer ([α]$_D$(MeOH) +41.7°, c=0.88) and then the (−)-enantiomer ([α]$_D$(MeOH) −39.8°, c=0.99).

EXAMPLE 6

5-[4-(5-Fluoro-2,3-dihydrobenzofuran-7-yl)-2-hydroxy-4-methyl-2-trifluoromethyl-pentylamino]isoquinoline Analogously to Example 1, 4-(5-fluoro-2,3-dihydrobenzofuran-7-yl)-2-hydroxy-4-methyl-2-trifluoromethyl-pentanal is converted with 5-aminoisoquinoline into 5-[4-(5-fluoro-2,3-dihydrobenzofuran-7-yl)-2-hydroxy-4-methyl-2-trifluoromethyl-pentylidenamino]isoquinoline, which is reduced with sodium borohydride to the product.

$^1$H-NMR (300 MHz, CDCl$_3$); δ=1.43 (s, 3H), 1.55 (s, 3H), 2.30 (d, 1H), 2.71 (d, 1H), 2.92 (m, 1H), 3.07 (m, 1H), 3.17 (dd, 1H), 3.35 (dd, 1H), 4.35 (br.t, 1H), 4.49 (q, 1H), 4.55 (q, 1H), 6.27 (m, 1H), 6.78 (dm, 1H), 6.88 (dm, 1H), 7.36 (m, 2H), 7.40 (d, 1H), 8.45 (d, 1H), 9.13 (s, 1H).

EXAMPLE 7

5-[4-(5-Fluoro-2,3-dihydrobenzofuran-7-yl)-2-hydroxy-4-methyl-2-trifluoromethyl-pentylamino]quinoline Analogously to Example 1, 4-(5-fluoro-2,3-dihydrobenzofuran-7-yl)-2-hydroxy-4-methyl-2-trifluoromethyl-pentanal is converted with 5-aminoquinoline into 5-[4-(5-fluoro-2,3-dihydrobenzofuran-7-yl)-2-hydroxy-4-methyl-2-trifluoromethyl-pentylidenamino]quinoline, which is reduced with sodium borohydride to the product.

$^1$H-NMR (300 MHz, CDCl$_3$); δ=1.43 (s, 3H), 1.54 (s, 3H), 2.31 (d, 1H), 2.68 (d, 1H), 2.96 (m, 1H), 3.08 (m, 1H), 3.17 (dd, 1H), 3.35 (dd, 1H), 4.32 (br.t, 1H), 4.52 (m, 2H), 6.15 (d, 1H), 6.80 (dm, 1H), 6.88 (dd, 1H), 7.31 (dd, 1H), 7.45 (t, 1H), 7.53 (d, 1H), 7.98 (d, 1H), 8.86 (dd, 1H).

EXAMPLE 8

5-[4-(2,3-Dihydro-5-fluoro-7-benzofuranyl)-2-hydroxy-4-methyl-2-trifluoromethyl-pentylamino]quinolin-2[1H]-one Analogously to Example 1, the corresponding imine is produced starting from 250 mg of 4-(2,3-dihydro-5-fluoro-7-benzofuranyl)-2-hydroxy-4-methyl-2-trifluoromethyl-pentanal and 124 mg of 5-aminoquinolin-2[1H]-one. After reaction with sodium cyanoborohydride, the title compound is obtained.

$^1$H-NMR (CD$_3$OD): δ=1.38 (s, 3H), 1.60 (s, 3H), 2.74-2.88 (m, 1H), 2.94-3.05 (m, 4H), 3.05-3.17 (m, 1H), 4.50 (t, 2H), 5.83 (d, 1H), 6.52 (d, 1H), 6.62-6.72 (m, 2H), 6.83 (dd, 1H), 7.22 (t, 1H), 7.94 (d, 1H)

EXAMPLE 9

6-Fluoro-5-[4-(5-fluoro-2,3-dihydrobenzofuran-7-yl)-2-hydroxy-4-methyl-2-trifluoromethyl-pentylamino]-2-methylquinoline Analogously to Example 1, the corresponding imine is produced starting from 250 mg of 4-(2,3-dihydro-5-fluoro-7-benzofuranyl)-2-hydroxy-4-methyl-2-trifluoromethyl-pentanal and 138 mg of 5-amino-6-fluoro-2-methylquinoline. After reaction with sodium cyanoborohydride, the title compound is obtained.

$^1$H-NMR (CD$_3$OD): δ=1.36 (s, 3H), 1.57 (s, 3H), 2.01 (d, 1H), 2.72 (s, 3H), 2.74-2.84 (m, 1H), 2.92 (d, 1H), 2.94-3.08 (m, 1H), 3.23 (d, 1H), 3.31 (d, 1H), 4.34-4.53 (m, 2H), 6.62 (d, 1H), 6.75 (dd, 1H), 7.34-7.49 (m, 3H), 8.19 (d, 1H)

EXAMPLE 10

8-Fluoro-5-[4-(5-Fluoro-2,3-dihydrobenzofuran-7-yl)-2-hydroxy-4-methyl-2-trifluoromethyl-pentylamino]-2-methylquinoline Analogously to Example 1, the corresponding imine is produced starting from 45 mg of 4-(2,3-dihydro-5-fluoro-7-benzofuranyl)-2-hydroxy-4-methyl-2-trifluoromethyl-pentanal and 25 mg of 5-amino-8-fluoro-2-methylquinoline. After reaction with sodium cyanoborohydride, the title compound is obtained.

$^1$H-NMR (CD$_3$OD): δ=1.38 (s, 3H), 1.62 (s, 3H), 2.01 (d, 1H), 2.53 (dt, 1H), 2.73 (s, 3H), 2.84-3.22 (m, 4H), 4.44 (dt, 2H), 5.90 (dd, 1H), 6.66 (dd, 1H), 6.82 (dd, 1H), 7.14 (dd, 1H), 7.40 (d, 1H), 8.21 (dd, 1H).

EXAMPLE 11

5-[4-(5-Fluoro-2,3-dihydrobenzofuran-7-yl)-2-hydroxy-4-methyl-2-trifluoromethyl-pentylamino]-2-methylisoquinol-1(2H)-one Analogously to Example 1, 4-(2,3-dihydro-5-fluoro-7-benzofuranyl)-2-hydroxy-4-methyl-2-trifluoromethyl-pentanal is converted with 5-amino-2-methylisoquinol-1(2H)- one into the corresponding imine. After reaction with sodium borohydride, the title compound is obtained.

$^1$H-NMR (CDCl$_3$): δ=1.40 (s, 3H), 1.55 (s, 3H), 2.25 (d, 1H), 2.65 (d, 1H), 2.95-3.30 (m, 4H), 3.60 (s, 3H), 4.00 (br, 1H), 4.50 (q, 1H), 4.55 (q, 1H), 6.25 (d, 1H), 6.30 (d, 1H), 6.80 (dm, 1H), 6.90 (dm, 1H), 7.05 (d, 1H), 7.25 (t, 1H), 7.85 (d, 1H).

The separation into enantiomers was carried out on a chiral column (Chiralpak AD-H 5 μ, eluants hexane/ethanol). The angles of rotation for the enantiomers are: [α]$_D$=+31.5±0.2 (c=1 methanol) and [α]$_D$=−32.4±0.1 (c=0.99 methanol)

EXAMPLE 12

5-[4-(5-Fluoro-2,3-dihydrobenzofuran-7-yl]-2-hydroxy-4-methyl-2-trifluoromethyl-pentylamino]-2-methylquinoline a)
2-Hydroxy-4-methyl-2-trifluoromethyl-pent-4-enoic acid ethyl ester 3.2 g of iron (III) chloride is suspended in 1000 ml of dichloromethane and cooled to −10° C. 100 g of trifluoroethyl pyruvate is added, and it is stirred for one hour. About 140 g of isobutene is condensed to about −50° C. while being cooled, and the mixture is stirred for five hours at −40° C. to −50° C., and stirring is continued overnight. After the usual aqueous working-up, the aqueous phases are combined and washed with dichloromethane, the organic phases are combined, mixed with activated carbon, stirred for 30 minutes, filtered and concentrated by evaporation. For additional purification, the product is taken up in a cyclohexane (100 ml)/methanol (120 ml) mixture, and the phases are separated. The product-containing methanol phase is concentrated by evaporation.

Yield: 118.0 g =89% of theory $^1$H-NMR (600 MHz, CDCl$_3$): δ=1.35 (t, 3H), 1.79 (s, 3H), 2.59 (d, 1H), 2.76 (d, 1H), 3.87 (s, 1H), 4.325 (dq, 1H), 4.365 (dq, 1H), 4.82 (s, 1H), 4.92 (s, 1H).

Enantiomer Separation:

200 mg of the ester that is obtained in 12a) is dissolved in 2 ml of hexane and separated in the 5 cm Prochrom unit (Chiralpak AD) at a counterpressure of 2 bar; eluant: hexane/0.1% trifluoroacetic acid. Two fractions are obtained.

Enantiomer I (eluted with the indicated HPLC methods first; Chiralpak AS250-0.46 mm: 7.58 minutes/Chiralpak AD-H-5μ: 6.8 minutes):

[α]$_D$=−6.1°±0.2° (c=0.944; CHCl$_3$)

Enantiomer II (eluted with the indicated HPLC methods as a 2$^{nd}$ compound; Chiralpak AS250-4.6 μ: 9.17 minutes/Chiralpak AD-H-5 μ: 8.2 minutes):

[α]$_D$=+5.9°+0.5° (c=1.072; CHCl$_3$)

b) 4-(5-Fluoro-2,3-dihydrobenzofuran-7-yl)-2-hydroxy-4-methyl-2-trifluoromethyl-valeric acid-ethyl ester 18.32 g of 5-fluoro-2,3-dihydrobenzofuran is introduced and cooled to 0° C. While being stirred vigorously, 11.77 g of aluminum (III) chloride is added in one portion. The temperature is maintained, and now 10.00 g of the compound produced in Example 12a) is slowly added in drops. The batch is allowed to come to room temperature, and stirring is continued for about 7 hours. 50 ml each of ethyl acetate and water are added and stirred for 15 minutes. After 5 ml of concentrated hydrochloric acid is added, the phases are separated, and the organic phase is absorptively precipitated with sodium bicarbonate solution. The organic phase is washed with water and saturated sodium chloride solution and concentrated by evaporation. After bulb tube distillation at 85° C./1 mbar and subsequent crystallization of the crude product (bottom) from ethanol (100 mol)/water (80 ml), 13.1 g=81% of theory of the reaction product is obtained. In addition, 8.51 g of 5-fluoro-2,3-dihydrobenzofuran (distillate) is recovered as a colorless liquid.

Melting point: 72.4° C.

$^1$H-NMR (600 MHz, CDCl$_3$): δ=1.21 (t, 3H), 1.35 (s, 3H), 1.40 (s, 3H), 2.43 (d, 1H), 2.745 (d, 1H), 3.15 (m, 2H), 3.56 (sbr, 1H), 3.73 (dq, 1H), 4.125 (dq, 1H), 4.58 (t, 2H), 6.68 (dd, 1H), 6.77 (dm, 1H). The ester that is obtained can then be further reacted as a racemate or else as a pure enantiomer, as described in, for example, WO 03/082827, to form the compounds of general formulas IIa and IIb.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 102004055633.4, filed Nov. 12, 2004, German application No. 102005020331.0 and U.S. Provisional Application Ser. No. 60/628,550, filed Nov. 18, 2004, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula (IIa) or (IIb)

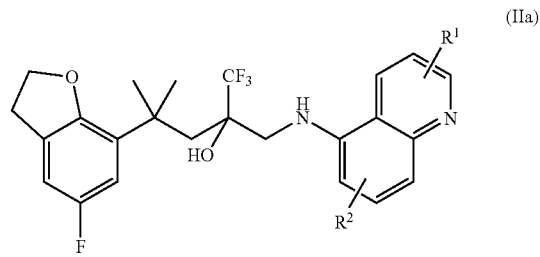
(IIa)

-continued

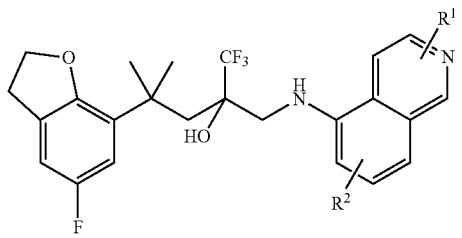
(IIb)

in which
R¹ and R², independently of one another, mean a hydrogen atom, a $C_{1-3}$-alkyl group, a halogen atom, a cyano group, a $C_{1-3}$-alkoxy group or a hydroxy group, or a racemate or a separately present stereoisomer thereof or a physiologically compatible salt thereof.

2. A compound of formula (IIa) or (IIb)

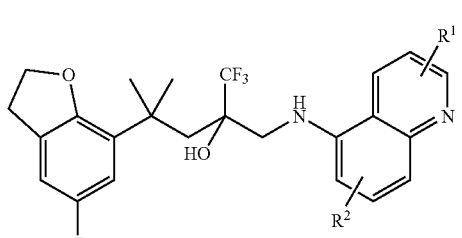
(IIa)

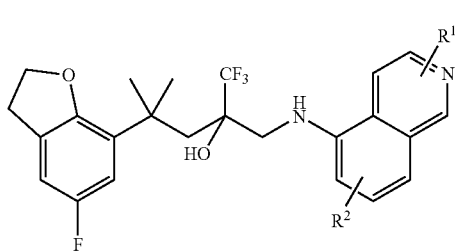
(IIb)

in which
R¹ and R², independently of one another, mean a hydrogen atom, a $C_{1-3}$-alkyl group, a halogen atom, a cyano, a $C_{1-3}$-alkoxy or a hydroxy group, or a racemate or a separately present stereoisomer thereof or a physiologically compatible salt or prodrug thereof.

3. The compound according to claim 1, which is 5-[4-(5-fluoro-2,3-dihydrobenzofuran-7-yl)-2-hydroxy-4-methyl-2-trifluoromethyl-pentylamino]-2-methylquinoline.

4. The compound according to claim 1, which is 5-[4-(5-fluoro-2,3-dihydrobenzofuran-7-yl)-2-hydroxy-4-methyl-2-trifluoromethyl-pentylamino]-1-methylisoquinoline.

5. The compound according to claim 1, which is 5-[4-(5-fluoro-2,3-dihydrobenzofuran-7-yl)-2-hydroxy-4-methyl-2-trifluoromethyl-pentylamino]isoquinol-1(2H)-one.

6. The compound according to claim 1, which is 5-[4-(5-fluoro-2,3-dihydrobenzofuran-7-yl)-2-hydroxy-4-methyl-2-trifluoromethyl-pentylamino]-2,6-dimethylquinoline.

7. The compound according to claim 1, which is 5-[4-(5-fluoro-2,3-dihydrobenzofuran-7-yl)-2-hydroxy-4-methyl-2-trifluorolnethyl-pentylamino]-6-chloro-2-methylquinoline.

8. The compound according to claim 1, which is 5-[4-(5-fluoro-2,3-dihydrobenzofuran-7-yl)-2-hydroxy-4-methyl-2-trifluoromethyl-pentylamino]isoquinoline.

9. The compound according to claim 1, which is 5-[4-(5-fluoro-2,3-dihydrohenzofuran-7-yl)-2-hydroxy-4-methyl-2-trifluoromethyl-pentylamino]quinoline.

10. The compound according to claim 1, which is 5-[4-(2,3-dihydro-5-fluoro-7-benzofuranyl)-2-hydroxy-4-methyl-2-trifluoromethyl-pentylamino]quinolin-2[1H]-one.

11. The compound according to claim 1, which is 6-fluoro-5-[4-(5-fluoro-2,3-dihydrobenzofuran-7-yl)-2-hydroxy-4-methyl-2-trifluoromethyl-pentylamino]-2-methylquinoline.

12. The compound according to claim 1, which is 8-fluoro-5-[4-(5-fluoro-2,3-dihydrobenzofuran-7-yl)-2-hydroxy-4-methyl-2-trifluoromethyl-pentylamino]-2-methylquinoline.

13. The compound according to claim 1, which is 5-[4-(5-fluoro-2,3-dihydrobenzofuran-7-yl)-2-hydroxy-4-methyl-2-trifluoromethyl-pentylamino]-2-methylisoquinol-1(2H)-one.

14. The (+)-enantiomer of the compound according to claim 3.

15. The (−)-enantiomer of the compound according to claim 3.

16. A process for preparing a compound of formula IIa or IIb according to claim 1 comprising reacting isobutene in the presence of a Lewis acid catalyst with trifluoroalkyl pyruvate to form a compound of formula XII

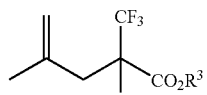
(XII)

wherein R³ means $C_1$-$C_5$-alkyl, the compound of formula XII is optionally subjected to an enantiomer separation and then is reacted as a chiral compound or as a racemate with 5-fluoro-2,3-dihydrobenzofuran

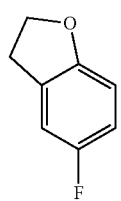

in a Friedel Crafts alkylation reaction to form a compound of formula X

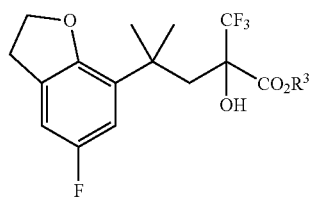
(X)

which is optionally subjected to an enantiomer separation, the compound of formula X— as a chiral compound or as a racemate—is either
reduced to form the alcohol of formula XI

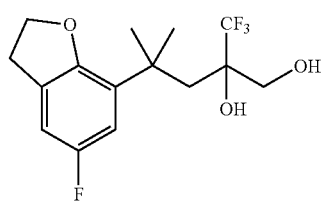
(XI)

and then oxidized to form the aldehyde of formula III

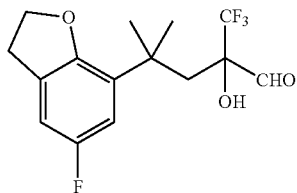
(III)

or compound X is reduced directly to form the aldehyde of formula III and then reacted to form the compound of formula IIa or IIb under conditions of reductive amination, optionally in two stages, with a 5-aminoquinoline derivative or with a 5-aminoisoquinoline derivative of one of the following formulae

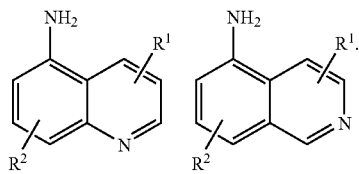

17. The process according to claim 16, wherein the enantiomer separation is carried out by column chromatography on a chiral phase.

18. The process according to claim 16, wherein a racemic intermediate stage from the synthesis is converted using a chiral adjuvant either into a diastereomer salt or into a diastereomer, then the diastereomer separation is performed, and a chiral auxiliary reagent is cleaved again.

19. The process according to claim 16, wherein an enantiomer separation is carried out at a stage of a compound of formula III, IV, V, VI, VII, VIII, IX, X or XI

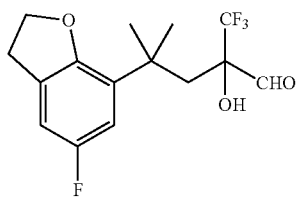
(III)

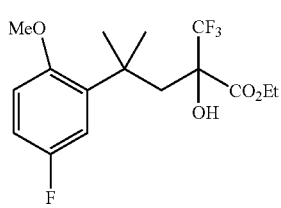
(IV)

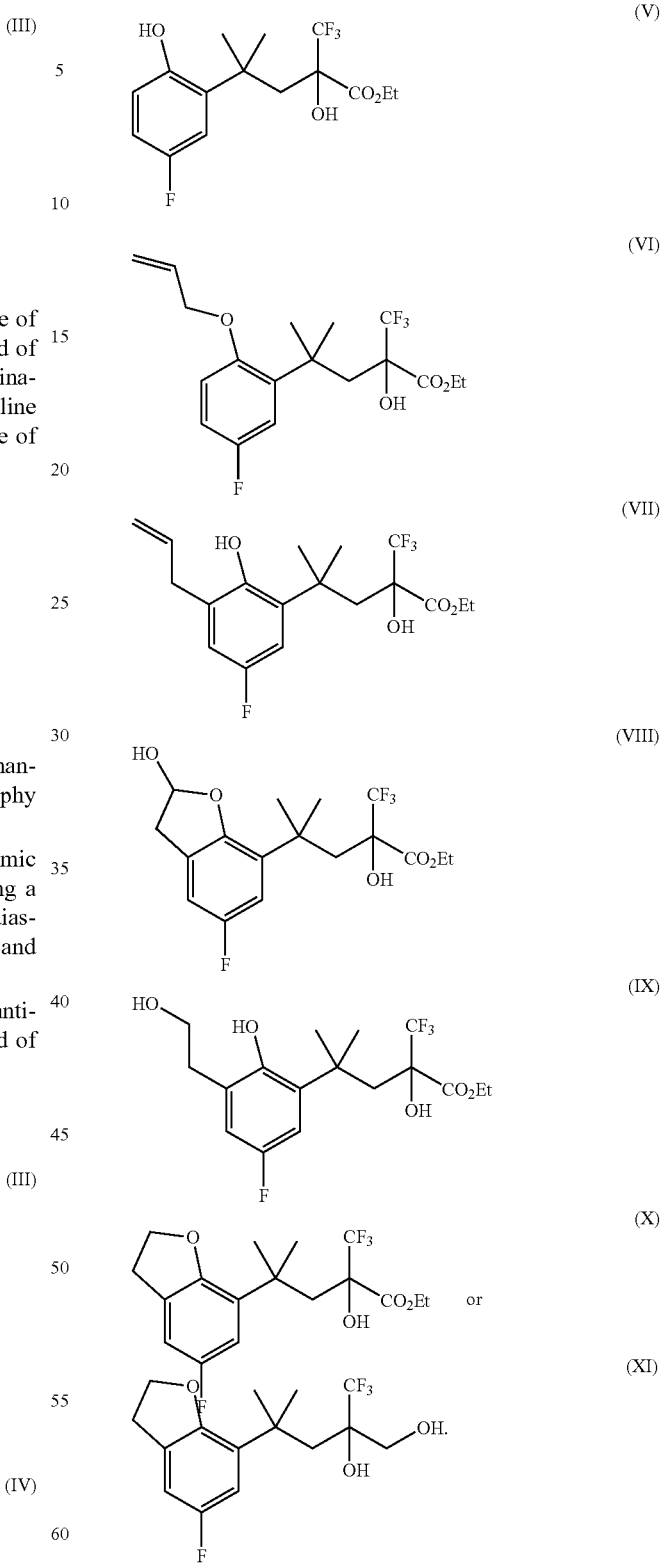

20. The process according to claim 18, wherein the chiral adjuvant is a chiral base, chiral diol, chiral alcohol or chiral acid.

21. A process for preparing a compound of formula IIa and or IIb according to claim 1, comprising reacting an aldehyde of formula III

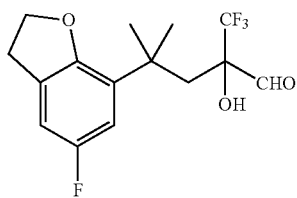
(III)

under conditions of reductive amination, optionally in two stages, with a 5-aminoquinoline derivative or with a 5-aminoisoquinoline derivative of one of the following formulae

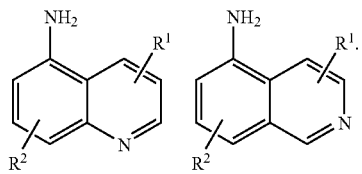

in which
R$^1$ and R$^2$, independently of one another, mean a hydrogen atom, a C$_{1-3}$-alkyl group, a halogen atom, a cyano group, a C$_{1-3}$-alkoxy group or a hydroxy group.

22. The process according to claim 21, wherein the compound of formula III is obtained either
by reduction of a compound of formula X—used as a chiral compound or as a racemate—

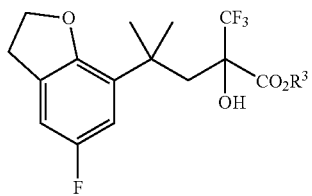
(X)

in which R$^3$ means C$_1$-C$_5$-alkyl, to form the alcohol of formula XI

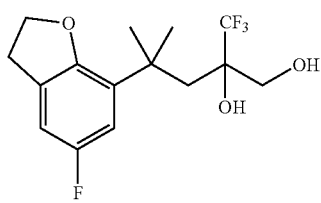
(XI)

and subsequent oxidation to form the aldehyde of formula III
or
by reduction of compound X—used as a chiral compound or as a racemate—directly to form the aldehyde of formula III

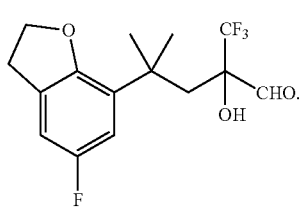
(III)

23. The process according to claim 22, wherein the compound of formula X is obtained from a compound of formula XII

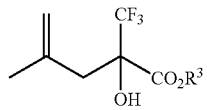
(XII)

wherein R$^3$ means C$_1$-C$_5$-alkyl, the compound of formula XII is optionally subjected to an enantiomer separation, then reacted as a chiral compound or as a racemate with 5-fluoro-2,3-dihydrobenzofuran

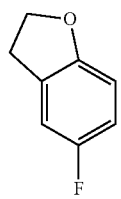

in a Friedel-Crafts alkylation reaction to form a compound of formula X

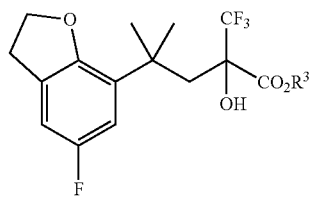
(X)

which is optionally subjected to an enantiomer separation.

24. The process according to claim 23, wherein the compound of formula XII is obtained by reacting isobutene in the presence of a Lewis acid catalyst with trifluoroalkyl pyruvate to form the compound of formula XII

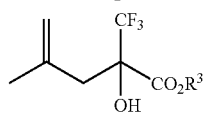
(XII)

wherein R$^3$ means C$_1$-C$_5$-alkyl,
the compound of formula XII is optionally subjected to an enantiomer separation.

25. The process according to claim 16, wherein the Lewis acid catalyst is chiral.

26. The process according to claim 14, wherein the starting materials are used in a chiral manner.

27. The process according to claim 22, wherein the intermediate products that are obtained in each case are subjected to an enantiomer separation or, after reaction with chiral adjuvants, to a diastereomer separation.

28. A method for treating an inflammatory disease comprising administering to a subject in need thereof an effective amount of a compound of claim 1.

29. A method according to claim 28, wherein the compound is administered locally.

30. A pharmaceutical composition comprising a compound according to claim 1 and a pharmaceutically acceptable carrier.

31. A pharmaceutical composition according to claim 30, which is suitable for local administration.

32. A compound according to claim 1, which is a salt of a compound of formula IIa or IIb.

* * * * *

UNITED STATES PATENT AND TRADEMARK OFFICE
CERTIFICATE OF CORRECTION

PATENT NO.        : 7,417,056 B2
APPLICATION NO.   : 11/272009
DATED             : August 26, 2008
INVENTOR(S)       : Stefan Jaroch Page 1 of 1

It is certified that error appears in the above-identified patent and that said Letters Patent is hereby corrected as shown below:

Column 23, line 63, reads "...dihydrohenzofuran..." should read
-- ...dihydrobenzofuran... --

Column 23, line 64, reads "trifluoronethyl..." should read -- trifluoromethyl... --

Column 24, line 2, reads "...dihydrohenzofuran..." should read
-- ...dihydrobenzofuran... --

Column 26, line 65, reads "formula IIa and" should read -- formula IIa --

Signed and Sealed this

Thirtieth Day of June, 2009

JOHN DOLL
*Acting Director of the United States Patent and Trademark Office*